United States Patent [19]
Bartsch

[11] Patent Number: 4,852,768
[45] Date of Patent: Aug. 1, 1989

[54] DOSING SYRINGE

[75] Inventor: Klaus Bartsch, Budenheim, Fed. Rep. of Germany

[73] Assignee: Blendax-Werke R. Schneider GmbH & Co., Fed. Rep. of Germany

[21] Appl. No.: 171,662

[22] Filed: Mar. 22, 1988

[30] Foreign Application Priority Data

Mar. 25, 1987 [DE] Fed. Rep. of Germany ....... 3709783

[51] Int. Cl.$^4$ .............................................. B67D 5/42
[52] U.S. Cl. ....................................... 222/46; 222/47; 222/39; 222/390; 604/211; 604/220; 604/224; 604/228
[58] Field of Search ................... 222/386, 390, 39, 23, 222/41, 47, 46; 604/207, 211, 218, 220, 222, 224, 228

[56] References Cited

U.S. PATENT DOCUMENTS

| 325,132 | 8/1885 | Tagliabue | 222/390 X |
|---|---|---|---|
| 1,668,196 | 5/1928 | Fageol | 222/390 X |
| 1,678,731 | 7/1928 | Klauset | 222/390 X |
| 1,694,767 | 12/1928 | Cook | 604/234 X |
| 2,771,217 | 11/1956 | Brown et al. | 604/211 X |
| 3,212,685 | 10/1965 | Swan et al. | 222/386 |
| 3,353,718 | 11/1967 | McLay | 222/390 X |
| 3,478,937 | 11/1969 | Solowey | 222/386 |
| 4,266,557 | 5/1981 | Merry | 604/222 X |
| 4,445,626 | 5/1984 | Steffen et al. | 222/39 |
| 4,704,105 | 11/1987 | Adorjan et al. | 604/222 |

FOREIGN PATENT DOCUMENTS

| 570724 | 2/1933 | Fed. Rep. of Germany | 222/390 |
|---|---|---|---|
| 575092 | 12/1923 | France | 222/390 |
| 579957 | 4/1924 | France | 222/390 |
| 577352 | 9/1924 | France | 222/390 |
| 812023 | 4/1937 | France | 222/390 |
| 80080 | 4/1934 | Sweden | 222/390 |
| 774172 | 5/1957 | United Kingdom | 222/390 |
| 1008505 | 10/1965 | United Kingdom | 222/390 |

Primary Examiner—Joseph J. Rolla
Assistant Examiner—Stephen B. Parker
Attorney, Agent, or Firm—Connolly and Hutz

[57] ABSTRACT

A dosing syringe has a cylindrical syringe body which at its tapering end has a dispensing orifice and at its other end a stepped cylindrical enlargement with two opposing handles. A recess is located below each handle, and a piston is inserted into the cylindrical syringe body. The piston is in contact with a dosing plunger having an external thread. Two threaded sides are arranged around the plunger and each threaded side has a positioning projection introduced into the recesses of the enlargement. According to the invention, the piston is connected to the dosing plunger by a spring retainer connection and the threaded sides have an outside groove in which an O-ring is inserted in countersunk fashion to hold the two threaded sides together. As a result, the piston-dosing unit can be prefabricated and introduced as a complete unit including the threaded sides into the enlargement of the syringe body where it is fixed simplifying the production technology of the dosing syringe.

1 Claim, 2 Drawing Sheets

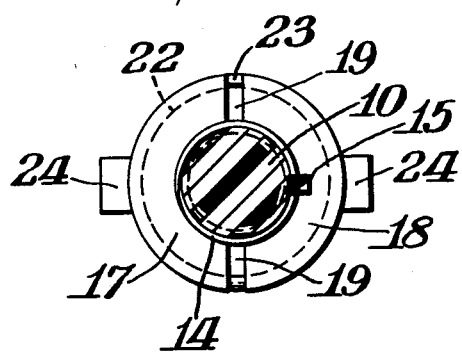
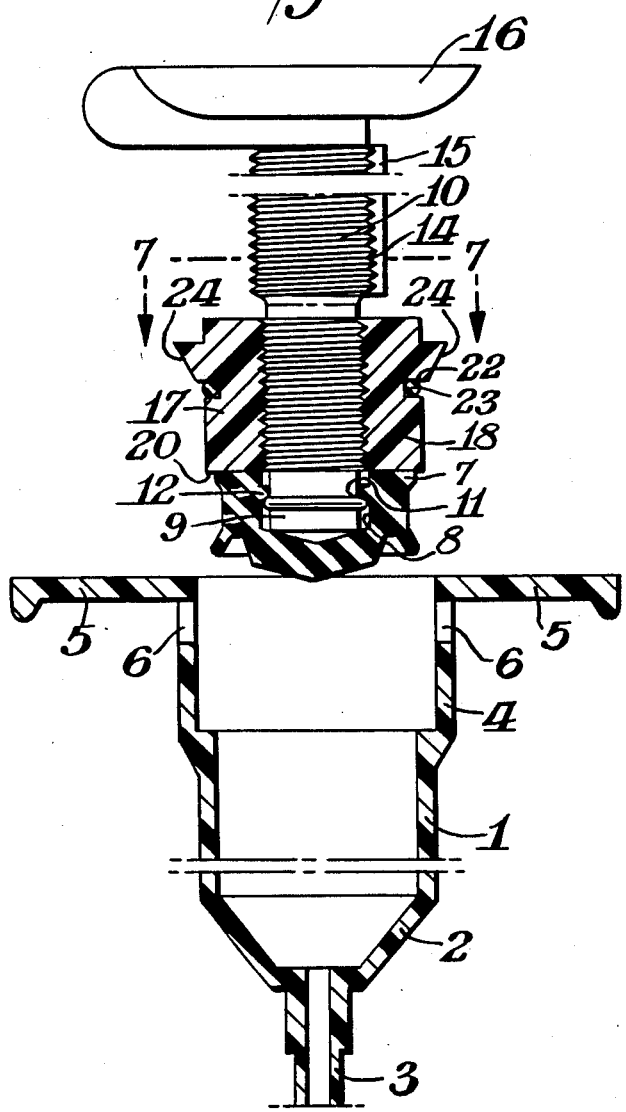

DOSING SYRINGE

BACKGROUND OF THE INVENTION

The present invention relates to a dosing syringe. Dosing syringes of known configuration often include a cylindrical syringe body which at its tapering end has a dispensing orifice and at its other end a stepped cylindrical enlargement with two opposing handles. Recesses are located below each handle. A piston is inserted from the enlarged end into the cylindrical syringe body. Two separate retainer sides each having an internal thread are positioned around a dosing plunger, the dosing plunger is rotatably arranged in the two-part retainer sides and these sides are located in the enlargement of the syringe body. Each piston has a positioning projection which can be introduced into the recesses of the enlargement.

In such a known, previously used dosing syringe, the piston is inserted after the syringe body has been filled. The two-part retainer sides having positioning projections thereon are inserted in the cylindrical enlargement and fixed by turning the dosing plunger in the thread of the threaded sides. This is accomplished in such a manner that the positioning projections are introduced into the recesses of the cylindrical enlargement.

The above described assembly of the dosing syringe which, in addition, must take place with a filled syringe body is cumbersome and time-consuming and involves the risk of contamination or spilling of the filling material.

SUMMARY OF THE INVENTION

Accordingly, it is an object of the present invention to improve a dosing syringe of the above mentioned type in such a way that the assembly of the dosing syringe is simplified and the risk of spilling or contamination of the material to be dispensed is prevented.

In accordance with the present invention, the piston of the dosing springe is connected to the dosing plunger by a spring retainer connection. Also, the two slightly spaced apart retainer sides which surround the plunger are held together around the plunger by an O-ring which fits within a complementary groove on the outside of each of the retainer sides.

BRIEF DESCRIPTION OF THE DRAWING

Novel features and advantages of the present invention in addition to those noted above will become apparent to those of ordinary skill in the art from a reading of the following detailed description in conjunction with the accompanying drawing wherein similar reference characters refer to similar parts and in which:

FIG. 6 is an exploded longitudinal sectional view of a modified dosing syringe, according to the present invention; and FIG. 7 is a sectional view taken along line 7—7 of FIG. 6.

DETAILED DESCRIPTION OF THE INVENTION

Figure 1:
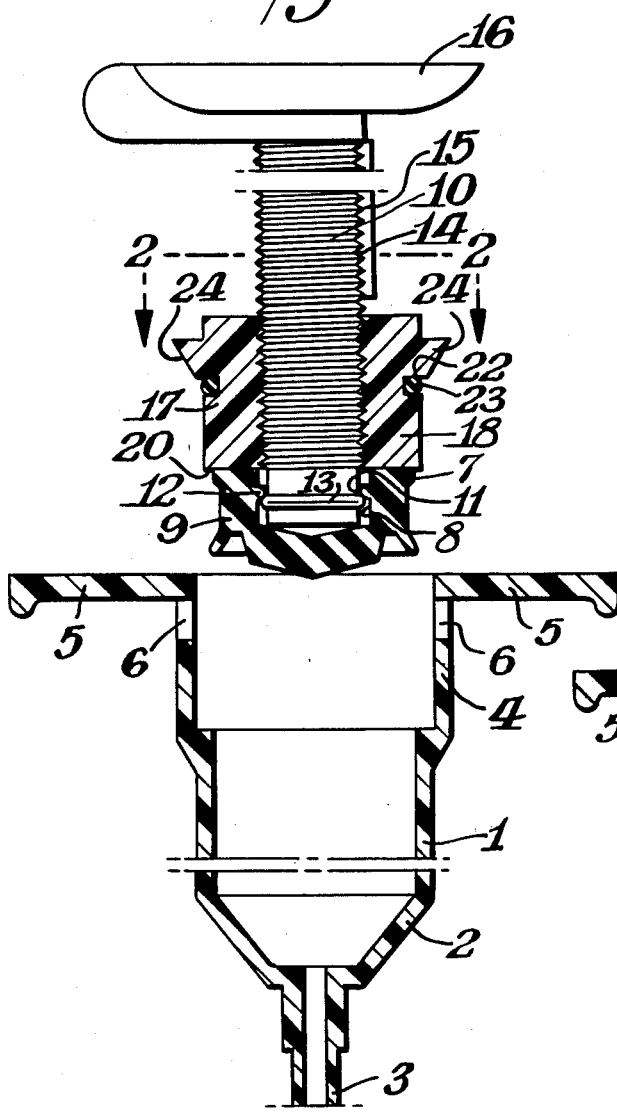
FIG. 1 is an exploded longitudinal sectional view of a dosing syringe, according to the present invention.
Figure 2:
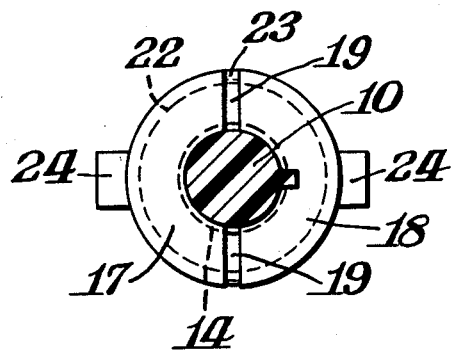
FIG. 2 is a sectional view taken along line 2—2 of FIG. 1.
Figure 3:
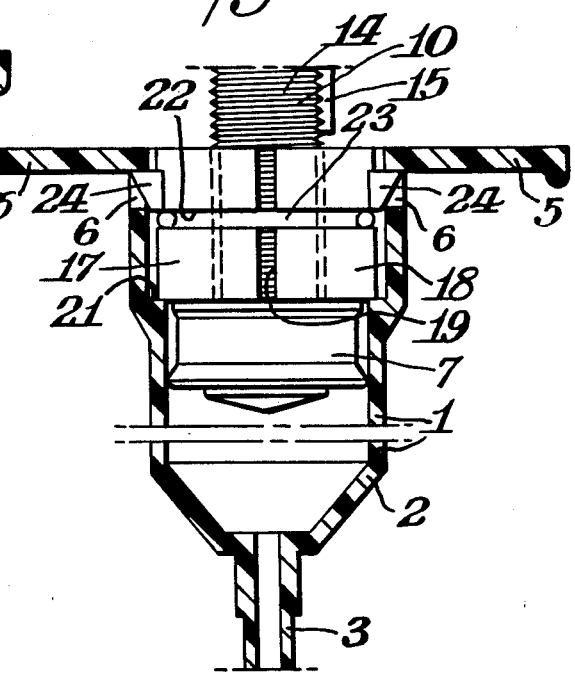
FIG. 3 is a longitudinal sectional view of the dosing syringe of FIG. 1 in assembled form.

Referring in more particularity to the drawing, FIGS. 1–3 illustrate a dosing syringe having a cylindrical syringe body 1. The syringe body 1 has a tapered end 2 with a dispensing orifice 3. The tapered end 2 may be suitably shaped for the installation of a seal and a syringe needle (not shown) or another dispensing nozzle adapted to the appropriate application of the dosing syringe. At the other end, the syringe body 1 has a stepped cylindrical enlargement 4 and two opposing handles 5 at its free end. The syringe body 1 with the dispensing orifice 3, the stepped cylindrical enlargement 4, and the handles 5 is manufactured as a single piece. A recess 6 is provided in the wall of the stepped cylindrical enlargement 4 directly under each of the opposed handles 5.

A piston 7 is constructed and arranged to fit within the cylindrical syringe body 1. The piston 7 has a central blind hole 8 into which a correspondingly shaped projection 9 of a dosing plunger 10 is snap fitted by means of a spring retainer connection 11. The spring retainer connection 11 may have any known shape. In the exemplified embodiment, the blind hole 8 and the projection 9 each have an annular rounded projection 12 and 13, respectively, which are offset from each other in such a way that when the free end of the projection 9 rests on the bottom of the blind hole 8, the annular rounded projection 12 of the blind hole 8 in the direction of insertion lies in front of the annular rounded projection 13 of the projection 9 which keeps projection 9 from slipping out of the blind hole 8.

Adjacent the projection 9, the dosing plunger 10 has a screw thread 14, a projecting longitudinal rib 15 and a handle 16 at the free end thereof. Two approximately semi-circular retainer sides 17, 18 are arranged around the central shaft of dosing plunger 10 and these sides are separated from each other by a small gap 19. The retainer sides 17, 18 have internal threads matching the external screw thread 14 of the dosing plunger 10. The lower edges of the retainer sides 17, 18 rest on an internal step 21 of the stepped enlargement 4 and the upper surfaces form a plane with the upper surface of the handles 5. In the outside surface which in cross section is semi-circular, each retainer side 17,18 has a groove 22 and an elastic O-ring 23 is positioned into the groove urging the retainer sides 17,18 together.

The retainer sides 17, 18 each have a wedge-shaped projection 24 on the outside surface intended for engagement into the recesses 6 in the syringe body 1 underneath the handles 5. The distance across the upper edges of the wedge-shaped projections 24 adjacent the handles, when resting against the thread of the dosing plunger 10, is selected somewhat larger than the small diameter of the cylindrical enlargement 4. The wedge-shaped projections while utilizing their elastic deformation, are pushed through the closed cylindrical part of the cylindrical enlargement 4 and do not expand outwardly until positioned in the recesses 6. This relationship guarantees a firm locking of the dosing plunger 10 with the piston thereof in place in the syringe body.

Figure 4:
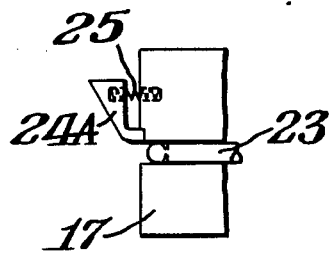
FIG. 4 is a partial elevational view of an alternate embodiment of the present invention.

It is also possible to arrange the wedge-shaped projection 24 as spring-loaded on the threaded sides 17, 18, such as shown in FIG. 4 at 24A. Projections 24A are fastened to the retainer sides 17, 18 by means of a hinge produced by material reduction. In this case, the dimensions of the projections 24A are not adapted so precisely to the small diameter of the cylindrical enlargement 4. However, cost of the injection molds in the production of these modified retainer sides 17, 18 is higher. Spring 25 is positioned between each projection 24A and its respective piston side.

Figure 5:
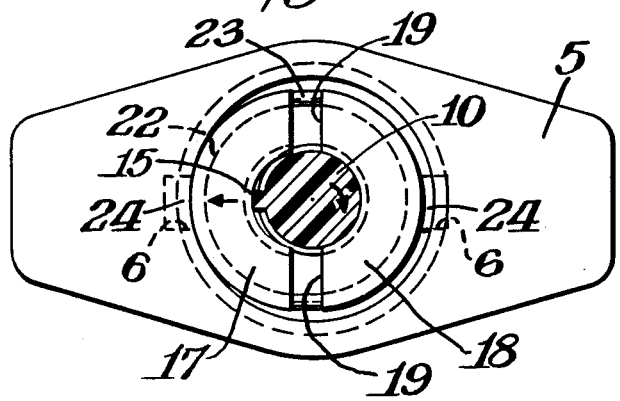
FIG. 5 is a cross-sectional view illustrating the piston sides within the syringe body the plunger turned midway through a metered dosing amount.

In use, once the plunger 10 and syringe body 1 are assembled with the projections 24 or 24A extending through the recesses or openings 6, turning of handle 6 urges the piston 11 in a downward direction toward dispersing orifice 3. Such movement expels the material disposed in the syringe body. Metered amounts of material are expelled through the orifice due to the relationship of rib 15 and the gaps 19 between the piston sides 17,18. With rib 15 positioned in one of the gaps 19, rotation of the plunger 10 urges the rib out of the gap and the sides 17,18 away from one another against the biasing force of elastic O-ring 23. Rotation of the plunger continues until the rib snaps into the opposite gap spaced 180° from the first gap. Hence, each 180° turn of the plunger 10 is easy to discern and such movement causes a metered amount of material to discharge from orifice 3. FIG. 5 shows the relationship of the parts midway through a half turn of the plunger.

According to the invention, it is now possible to arrange the retainer sides 17 and 18 opposite each other with their internal threads mating with the external thread 14 of the dosing plunger 10, and to hold these sides together by means of the O-ring 23 inserted into grooves 22. This may be done after or before the piston 7 is pushed onto the dosing plunger 10 for reciprocal fastening by the spring retainer connection 11. As a result, a prefabricated piston-plunger is obtained which after the syringe body 1 has been filled only has to be inserted in the upper end of the syringe body 1 in such a way that the wedge-shaped projections 24 of the retainer sides 17,18 snap into the recesses or openings 6 to fix the piston-plunger in the syringe body 1. By turning the dosing plunger 10 in the threads of the retainer sides 17,18 as explained above only the zero position has to be adjusted. Thereafter, perceivable half turns of the plunger produce specific amounts of material to discharge from the orifice. As a result of the invention, the assembly of the individual components of the piston-plunger can take place more conveniently and the manipulations with the filled syringe body can be limited to a minimum so that the risk of spilling and the penetration of contamination are minimized.

FIGS. 6 and 7 illustrate a dosing syringe similar in many respects to the syringe illustrated in FIGS. 1-3, and similar reference characters are used to identify similar parts. The dosing syringe of FIGS. 6 and 7 is different from the one shown in FIGS. 1-3 in that the threaded plunger 10 includes a large diameter portion next to handle 16 and a smaller diameter portion at the terminal end of the plunger. Longitudinal rib 15 extends outwardly from the large diameter portion of plunger 10. Operation of the dosing syringe shown in FIGS. 6 and 7 is the same as the operation of the syringe shown in FIGS. 1-3.

What is claimed is:

1. A dosing syringe comprising a cylindrical syringe body having a tapering end with a dispensing orifice therein, a stepped cylindrical enlargement, two opposing handles connected to and extending from the cylindrical enlargement, two opposing recesses in the cylindrical enlargement one underneath each handle, a piston inserted into the cylindrical syringe body from the enlarged end thereof, two retainer sides each having an internal thread, and a dosing plunger having an external thread, the dosing plunger being rotatably arranged in the two-part retainer sides with the threads engaging one another and the two retainer sides positioned in the enlargement of the syringe body, each retainer side having a positioning projection fitted into the recesses in the enlargement, a spring retainer connection releasably connecting the piston to the dosing plunger, each of the retainer sides having an outside groove, and an O-ring in the groove holding the two retainer sides together, and wherein the retainer sides are slightly spaced apart forming a pair of gaps 180° from each other, and a longitudinal rib on the plunger constructed and arranged to fit into one of the gaps and to be movable to the other gap upon 180° rotation of the dosing plunger.

* * * * *